United States Patent
Maione et al.

(10) Patent No.: US 10,975,121 B2
(45) Date of Patent: *Apr. 13, 2021

(54) ANALGESIC MU-OPIOID RECEPTOR BINDING PEPTIDE PHARMACEUTICAL FORMULATIONS AND USES THEREOF

(71) Applicant: Cytogel Pharma, LLC, Darien, CT (US)

(72) Inventors: Theodore E. Maione, Green Island, NY (US); Constantine Basil Maglaris, New Canaan, CT (US)

(73) Assignee: CYTOGEL PHARMA, LLC, Darien, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/962,200

(22) Filed: Apr. 25, 2018

(65) Prior Publication Data

US 2018/0371017 A1    Dec. 27, 2018

Related U.S. Application Data

(60) Provisional application No. 62/592,601, filed on Nov. 30, 2017, provisional application No. 62/524,491, filed on Jun. 24, 2017.

(51) Int. Cl.
| | | |
|---|---|---|
| *C07K 5/107* | (2006.01) | |
| *A61K 47/40* | (2006.01) | |
| *A61K 38/07* | (2006.01) | |
| *A61K 47/69* | (2017.01) | |
| *A61K 47/61* | (2017.01) | |
| *A61K 9/08* | (2006.01) | |
| *A61K 31/724* | (2006.01) | |

(52) U.S. Cl.
CPC ............. *C07K 5/1016* (2013.01); *A61K 9/08* (2013.01); *A61K 31/724* (2013.01); *A61K 38/07* (2013.01); *A61K 47/40* (2013.01); *A61K 47/61* (2017.08); *A61K 47/6951* (2017.08)

(58) Field of Classification Search
None
See application file for complete search history.

(56) References Cited

U.S. PATENT DOCUMENTS

| | | |
|---|---|---|
| 4,663,160 A | 5/1987 | Tsay et al. |
| 4,684,620 A | 8/1987 | Hruby et al. |
| 5,410,016 A | 4/1995 | Hubbell et al. |
| 5,885,958 A | 3/1999 | Zadina et al. |
| 6,107,358 A | 8/2000 | Harada et al. |
| 6,303,578 B1 | 10/2001 | Zadina et al. |
| 6,337,207 B1 | 1/2002 | Kreek et al. |
| 6,514,710 B1 | 2/2003 | Jones et al. |
| 6,592,895 B2 | 7/2003 | Lang et al. |
| 6,740,639 B1 | 5/2004 | Dwivedi et al. |
| 8,940,704 B2 * | 1/2015 | Maione .................... C07K 5/10 514/21.9 |
| 2003/0068672 A1 | 4/2003 | Yu |
| 2003/0139446 A1 | 7/2003 | Chen et al. |
| 2003/0147835 A1 | 8/2003 | Munro et al. |
| 2004/0266805 A1 | 12/2004 | Jessop et al. |
| 2011/0065648 A1 * | 3/2011 | Maione .................... A61K 9/08 514/18.4 |
| 2011/0287040 A1 * | 11/2011 | Maione ................. A61K 38/07 424/185.1 |
| 2012/0322740 A1 | 12/2012 | Zadina et al. |
| 2016/0264625 A1 | 9/2016 | Maione |
| 2018/0251490 A1 * | 9/2018 | Maione .................... A61K 9/08 |
| 2018/0282370 A1 * | 10/2018 | Maione ................ C07K 5/1016 |
| 2018/0291060 A1 * | 10/2018 | Maione .................... C07K 5/10 |
| 2018/0311303 A1 * | 11/2018 | Maione ................. A61K 38/07 |

FOREIGN PATENT DOCUMENTS

| | | |
|---|---|---|
| EP | 1174152 A1 | 1/2002 |
| EP | 2236496 A2 | 10/2010 |
| JP | 10330398 A | 12/1998 |
| WO | 9842732 A1 | 10/1998 |
| WO | 0060956 A1 | 10/2000 |
| WO | 02102833 A1 | 12/2002 |
| WO | 03020304 A2 | 3/2003 |
| WO | 2006068768 A2 | 6/2006 |
| WO | 2009033740 A2 | 3/2009 |
| WO | 2009076672 A1 | 6/2009 |
| WO | 2009084493 A1 | 7/2009 |
| WO | 2011034659 A2 | 3/2011 |
| WO | 2011146922 A2 | 11/2011 |

OTHER PUBLICATIONS

Foran et al. "A substance P-opioid chimeric peptide as a unique nontolerance-forming analgesic" Proc. Natl. Acad. Sci. 97:7621-7626. (Year: 2000).*
Skoubis, P.D., et al., "Naloxone Fails to Produce Conditioned Place Aversion in mu-opioid Receptor Knock-Out Mice." Neuroscience, 2001, 106(4): 757-763.
Snider, R.H., et al., "Procalcitonin and its Component Peptides in Systemic Inflammation: Immunochemical Characterization." Journal of Investigative Medicine, 1997, 45(9): 552-560.
Verghese, S.T., et al., "Acute pain management in children." Journal of Pain Reearch, 2010, 3: 105-123.
Watanabe, H., et al., "Differential inhibitroy effects of mu-opioids on substance P- and capsaicin-induced nociceptive behavior in mice." Peptide, 2006, 27: 760-768.
Webster, L.R., et al., "Predicting Aberrant Behaviors in Opioid-Treated Patients: Preliminary Validation of the Opioid Risk Tool." Pain Medicine, 2005, 6(6): 432-442.

(Continued)

*Primary Examiner* — Sudhakar Katakam
*Assistant Examiner* — Zachary J Miknis
(74) *Attorney, Agent, or Firm* — Saliwanchik, Lloyd & Eisenschenk

(57) ABSTRACT

The subject invention provides compositions and methods for alleviating pain. Specifically, the subject invention provides pharmaceutical formulations of peptides, and/or their salts, having advantageous μ-opioid receptor binding activity.

1 Claim, No Drawings

Specification includes a Sequence Listing.

(56) References Cited

OTHER PUBLICATIONS

Wu, D., et al., "Synthesis, characterization and drug release from three-arm poly(e-caprolactone) maleic acid / poly (ethylene glycol) diacrylate hydrogels." J. Biomater. Sci. Polymer Edn, 2003, 14(8): 777-802.
Yoo, J.S., et al., "Novel pH and Temperature-Sensitive Block Copolymers: Poly(ethylene glycol)-b-poly(ε-caprolactone)-bpoly(β-amino ester)." Macromolecular Research, 2006, 14(1): 117-120.
Youan, B.B.C., et al., "Evaluation of Sucrose Esters as Alternative Surfactants in Microencapsulation of Proteins by the Solvent Evaporation Method." AAPS PharmSci, 2003, 5(2): 1-9.
Zadina, J.E., et al., "A potent and selective endogenous agonist for the mu-opiate receptor." Nature, 1997, 386, 499-502.
Zhao, S., et al., "Synthesis and Characterization of Biodegradable Thermo- and pH-Sensitive Hydrogels Based on Pluronic F127/Poly(ε-caprolactone) Macromer and Acrylic Acid." Macromolecular Research, 2009, 17(12): 1025-1031.
Abbadie, C., et al., "Anatomical and functional correlation of the endomorphins with mu opioid receptor splice variants." European Journal of Neuroscience, 2002, 16: 1075-1082.
Agnes, R.S., et al., "Structure-Activity Relationships of Bifunctional Peptides Based on Overlapping Pharmacophores at Opioid and Cholecystokinin Receptors." J. MEd. Chem., 2006, 49: 2868-2875.
Alstergren, P., et al., "Co-Variation of Neuropeptide Y, Calcitonin Gene-related Peptide, Substance P and Neurokinin A in Joint Fluid from Patients with Temporomandibular Joint Arthritis." Archs oral Biol., 1995, 40(2): 127-135.
Avidor-Reiss, T., et al., "Adenylylcyclase Supersensitization in mu-Opioid Receptor-transfected Chinese Hamster Ovary Cells Following Chronic Opioid Treatment." The Journal of Biological Chemistry, 1995, 270(50): 29732-29738.
Bansal, A.K., et al., "Salt Selection in Drug Development." Pharmaceutical Technology, 2008, 32(3): 1-12.
Batchelor, H., "Paediatric pharmacokinetics: key considerations." British Journal of Clinical Pharmacology, 2013, 79(3): 395-404.
Berge, S.M., et al., "Pharmaceutical Salts." Journal of Pharmaceutical Sciences, Jan. 1977, 66(1): 1-19.
Berger, A., et al., "How to Design an Opioid Drug That Causes Reduced Tolerance and Dependence." Ann Neurol, 2010, 67:559-569.
Border, W.A., et al., "Induction of Membranous Nephropathy in Rabbits by Administration of an Exogenous Cationic Antigen." J. Clin. Invest., Feb. 1982, 69: 451-461.
Borzsei, R., et al., "Inhibitory Action of Endomorphin-1 on Sensory Neuropeptide Release and Neurogenic Inflammation in Rats and Mice." Neuroscience, 2008, 152: 82-88.
Cardillo, G., et al., "Endomorphin-1 Analogues Containing Beta-Proline Are Mu-Opioid Receptor Agonists and Display Enhanced Enzymatic Hydrolysis Resistance." J. Med. Chem., 2002, 45: 2571-2578.
Cardillo, G., et al., "Stability against enzymatic hydrolysis of endomorphin-1 analogues containing Beta-proline." Org. Biomol. Chem., 2003, 1: 1498-1502.
Cardillo, G., et al., "Synthesis and Evaluation of the Affinity toward Mu-Opioid Receptors of Atypical, Lipophilic Ligands Based on the Sequence c[-Tyr-Pro-Trp-Phe-Gly-]." J. Med. Chem., 2004, 47: 5198-5203.
Cardillo, G., et al., "Synthesis and Binding Activity of Endomorphin-1 Analogues Containing Beta-Amino Acids." Bioorganic & Medicinal Chemistry Letters, 2000, 10: 2755-2758.
Chalmers, J., "Hypertension Optimal Treatment (HOT) study: a brilliant concept, but a qualified success." Journal of Hypertension, 1998, 16: 1403-1405.
Cho, C.S., et al., Clonazepam release from bioerodible hydrogels based on semi-interpenetrating polymer networks composed of poly(E-caprolactone) and poly(ethylene glycol) macromer. International Journal of Pharmaceutics, 1999, 18: 235-242.
Cornish, J., et al., "Trifluoroacetate, a contaminant in purified proteins, inhibits proliferation of osteoblasts and chondrocytes." the American Physiological Society, 1999, 277(5): E779-E783.
Cruise, G.M., et al., "Characterization of permeability and network structure of interfacially photopolymerized poly(ethylene glycol) diacrylate hydrogels." Biomaterials, 1998, 19: 1287-1294.
Czapla, M.A., et al., "Differential Cardiorespiratory Effects of Endomorphin 1, Endomorphin 2, DAMGO, and Morphine." Am J Respir Crit Care Med, 2000, 162: 994-999.
Davies, G., "Changing the Salt, Changing the Drug." Pharmaceutical Journal, 2001, 266(7138): 322-323.
Ferro, A., "Paediatric prescribing: why children are not small adults." British Journal of Clinical Pharmacology, 2014, 79(3): 351-353.
Finn, A.K., et al., "Endocytosis of the Mu Opioid Receptor Reduces Tolerance and a Cellular Hallmark of Opiate Withdrawal." Neuron, 2001, 32: 829-839.
Gould, P.L . . . , "Salt selection for basic drugs." International Journal of Pharmaceutics, 1986, 33: 201-217.
Heller, J., et al., "Injectable Semi-Solid Poly (Ortho Esters) for the Controlled Delivery of Therapeutic Agents: Synthesis and Applications." Drug Deliv Technol, 2002, 2(1): 38-40.
Jain, G., et al., "Long-Term Neuropsychological Effects of Opioid Use n Children: A Descriptive Literature Review." Pain Physician, 2014, 17: 107-118.
Janecka, A., et al., "Synthesis and antinociceptive activity of cyclic endomorphin-2 and morphiceptin analogs." Biochemical Pharmacology, 2005, 71: 188-195.
Janecka, A., et al., "Enzymatic degradation studies of endomorphin-2 and its analogs containing N-methylated amino acids." Peptide, 2006, 27: 131-135.
Jeong, B., et al., "Thermoreversible Gelatin of PEG-PLGA-PEG Triblock Copolymer Aqueous Solutions." Macromolecules, 1999, 32: 7064-7069.
Jessop, D.S., "Endomorphins as Agents for the Treatment of Chronic Inflammatory Disease." BioDrugs, 2006, 20(3): 161-166.
Jessop, D.S., et al., "Endomorphins in rheumatoid arthritis, osteoarthritis, and experimental arthritis." Ann. N.Y. Acad. Sci., 2010, 1193(1): 117-122.
Kanaoka, S., et al., "Star-Shaped Polymers by Living Cationic Polymerization. 2. Synthesis of Amphiphilic Star-Shaped Block Polymers of Vinyl Ethers with Hydroxyl Groups." Macromolecules, Oct. 1991, 24(21): 5741-5745.
Kanaoka, S., et al., "Star-Shaped Polymers by Living Cationic Polymerization. 5. Core-Functionalized Amphiphilic Star-Shaped Polymers of Vinyl Ethers with Hydroxyl Groups: Synthesis and Host-Guest Interaction." Macromolecules, 1993, 26: 254-259.
Khalil, Z., et al., "Modulation of peripheral inflammation by locally administered endomorphin-1." Inflamm. res., 1999, 48: 550-556.
Kim, S.Y., et al., "Methoxy poly(ethylene glycol) and e-caprolactone amphiphilic block copolymeric micelle containing indomethacin. II. Micelle formation and drug release behaviours." Journal of Controlled Release, 1998, 51: 13-22.
Lang, M., et al., "Synthesis and structural analysis of functionalized poly (e-caprolactone)-based three-arm star polymers." Journal of Polymer Science Part A: Polymer Chemistry, 2002, 40(8): 1127-1141.
Madhavan, A., et al., "Opioid-induced GABA potentiation after chronic morphine attenuates the rewarding effects of opioids in the ventral tegmental area." J Neurosci., 2010, 30(42): 14029-14035.
Madhavan, A., et al., "μ-Opioid Receptor Endocytosis Prevents Adaptations in Ventral Tegmental Area GABA Transmission Induced during Naloxone-Precipitated Morphine Withdrawal." J Neurosci., 2010, 30(9): 3276-3286.
Majumdar, S. ,et al., "Truncated G protein-coupled mu opioid receptor MOR-1 splice variants are targets for highly potent opioid analgesics lacking side effects." PNAS, 2011, 108(49): 19778-19783.
McDougall, J.J., et al., "Attenuation of Knee Joint Inflammation by Peripherally Administered Endomorphin-1." Journal of Molecular Neuroscience, 2004, 22: 125-137.
McPherson, A., "A comparison of salts for the crystallization of macromolecules." Protein Science, 2001, 10: 418-422.

(56) References Cited

OTHER PUBLICATIONS

Neumeyer, J.L., et al., "New Opioid Designed Multiple Ligand from Dmt-Tic and Morphinan Pharmacophores." J. Med. Chem., 2006, 49: 5640-5643.

Nguyen, K.T., et al., "Photopolymerizable hydrogels for tissue engineering applications." Biomaterials, 2002, 23: 4307-4314.

Pan, Y.X., et al., "Identification of Four Novel Exon 5 Splice Variants of the Mouse mu-Opioid Receptor Gene: Functional Consequences of C-Terminal Splicing." Molecular Pharmacology, 2005, 68(3): 866-875.

Peppas, N.A., et al., "Hydrogels in pharmaceutical formulations." European Journal of Pharmaceutics and Biopharmaceutics, 2000, 50: 27-46.

Peppas, N.A., et al., "Hydrogels as mucoadhesive and bioadhesive materials: a review." Biomaterials, 1996, 17: 1553-1561.

Price, C., "Micelle Formation by Block CoPolymers in Organic Solvents." Pure & Appl. Chem., 1983, 55(10): 1563-1572.

Qiu, Z., et al., "Miscibility and crystallization of poly(ethylene oxide) and poly(e-caprolactone) blends." Polymer, 2003, 44:3101-3106.

Roux, S., et al., "Elimination and exchange of trifluoroacetate counter-ion from cationic peptides: a critical evaluation of different approaches." Journal of Peptide Science, 2008, 14: 354-359.

Schiess, M.C., et al., "The effects of CGRP on calcium transients of dedifferentiating cultured adult rat cardiomyocytes compared to non-cultured adult cardiomyocytes: possible protective and deleterious results in cardiac function." Peptides, 2005, 26: 525-530.

Shuai, X., et al., "Micellar carriers based on block copolymers of poly(e-caprolactone) and poly(ethylene glycol) for doxorubicin delivery." Journal of Controlled Release, 2004, 98: 415-426.

\* cited by examiner

SEQUENCE LISTING

```
<160> NUMBER OF SEQ ID NOS: 26

<210> SEQ ID NO 1
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: Phe-NH2 (phenylalanine amide)

<400> SEQUENCE: 1

Tyr Pro Trp Xaa
1

<210> SEQ ID NO 2
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: Phe-NH2 (phenylalanine amide)

<400> SEQUENCE: 2

Tyr Pro Phe Xaa
1

<210> SEQ ID NO 3
<211> LENGTH: 4
<212> TYPE: PRT
<213> ORGANISM: Artificial sequence
<220> FEATURE:
<223> OTHER INFORMATION: peptide

<400> SEQUENCE: 3

Tyr Pro Trp Phe
1
```

```
<210> SEQ ID NO 4
<211> LENGTH: 4
<212> TYPE: PRT
<213> ORGANISM: Artificial sequence
<220> FEATURE:
<223> OTHER INFORMATION: peptide

<400> SEQUENCE: 4

Tyr Pro Phe Phe
1

<210> SEQ ID NO 5
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: D-Phe-NH2 (D-phenylalanine amide)

<400> SEQUENCE: 5

Tyr Pro Trp Xaa
1

<210> SEQ ID NO 6
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: D-Phe-NH2 (D-phenylalanine amide)

<400> SEQUENCE: 6

Tyr Pro Phe Xaa
1

<210> SEQ ID NO 7
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: pNO2-Phe-NH2 (p-nitrophenylalanine amide)

<400> SEQUENCE: 7

Tyr Pro Trp Xaa
1

<210> SEQ ID NO 8
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: pNO2-Phe-NH2 (p-nitrophenylalanine amide)

<400> SEQUENCE: 8

Tyr Pro Phe Xaa
1
```

```
<210> SEQ ID NO 9
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: N-Me-Phe (N-methyl phenylalanine)
<220> FEATURE:
<221> NAME/KEY: MISC_FEATURE
<222> LOCATION: (4)..(4)
<223> OTHER INFORMATION: Phe-NH2 (phenylalanine amide)

<400> SEQUENCE: 9

Tyr Pro Xaa Xaa
1

<210> SEQ ID NO 10
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: N-Et-Phe (N-ethyl phenylalanine)
<220> FEATURE:
<221> NAME/KEY: MISC_FEATURE
<222> LOCATION: (4)..(4)
<223> OTHER INFORMATION: Phe-NH2 (phenylalanine amide)

<400> SEQUENCE: 10

Tyr Pro Xaa Xaa
1

<210> SEQ ID NO 11
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: N-Me-Phe (N-methyl phenylalanine)
<220> FEATURE:
<221> NAME/KEY: MISC_FEATURE
<222> LOCATION: (4)..(4)
<223> OTHER INFORMATION: D-Phe-NH2 (D-phenylalanine amide)

<400> SEQUENCE: 11

Tyr Pro Xaa Xaa
1

<210> SEQ ID NO 12
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: N-Et-Phe (N-ethyl phenylalanine)
<220> FEATURE:
<221> NAME/KEY: MISC_FEATURE
<222> LOCATION: (4)..(4)
<223> OTHER INFORMATION: D-Phe-NH2 (D-phenylalanine amide)
```

```
<400> SEQUENCE: 12

Tyr Pro Xaa Xaa
1

<210> SEQ ID NO 13
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Lys (D-Lysine)

<400> SEQUENCE: 13

Tyr Xaa Trp Phe
1

<210> SEQ ID NO 14
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Lys (D-Lysine)

<400> SEQUENCE: 14

Tyr Xaa Phe Phe
1

<210> SEQ ID NO 15
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Orn (D-Ornithine)

<400> SEQUENCE: 15

Tyr Xaa Trp Phe
1

<210> SEQ ID NO 16
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Orn (D-Ornithine)

<400> SEQUENCE: 16

Tyr Xaa Phe Phe
1

<210> SEQ ID NO 17
<211> LENGTH: 4
<212> TYPE: PRT
<213> ORGANISM: Artificial sequence
```

```
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Lys (D-Lysine)
<220> FEATURE:
<221> NAME/KEY: MISC_FEATURE
<222> LOCATION: (4)..(4)
<223> OTHER INFORMATION: pNO2-Phe (p-nitrophenylalanine)

<400> SEQUENCE: 17

Tyr Xaa Trp Xaa
1

<210> SEQ ID NO 18
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Lys (D-Lysine)
<220> FEATURE:
<221> NAME/KEY: MISC_FEATURE
<222> LOCATION: (4)..(4)
<223> OTHER INFORMATION: pNO2-Phe (p-nitrophenylalanine)

<400> SEQUENCE: 18

Tyr Xaa Phe Xaa
1

<210> SEQ ID NO 19
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Orn (D-Ornithine)
<220> FEATURE:
<221> NAME/KEY: MISC_FEATURE
<222> LOCATION: (4)..(4)
<223> OTHER INFORMATION: pNO2-Phe (p-nitrophenylalanine)

<400> SEQUENCE: 19

Tyr Xaa Trp Xaa
1

<210> SEQ ID NO 20
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Orn (D-Ornithine)
<220> FEATURE:
<221> NAME/KEY: MISC_FEATURE
<222> LOCATION: (4)..(4)
<223> OTHER INFORMATION: pNO2-Phe (p-nitrophenylalanine)

<400> SEQUENCE: 20

Tyr Xaa Phe Xaa
1
```

```
<210> SEQ ID NO 21
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Lys (D-Lysine)
<220> FEATURE:
<221> NAME/KEY: MISC_FEATURE
<222> LOCATION: (3)..(3)
<223> OTHER INFORMATION: N-Me-Phe (N-methyl phenylalanine)

<400> SEQUENCE: 21

Tyr Xaa Xaa Phe
1

<210> SEQ ID NO 22
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Orn (D-Ornithine)
<220> FEATURE:
<221> NAME/KEY: MISC_FEATURE
<222> LOCATION: (3)..(3)
<223> OTHER INFORMATION: N-Me-Phe (N-methyl phenylalanine)

<400> SEQUENCE: 22

Tyr Xaa Xaa Phe
1

<210> SEQ ID NO 23
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Lys (D-Lysine)
<220> FEATURE:
<221> NAME/KEY: MISC_FEATURE
<222> LOCATION: (3)..(3)
<223> OTHER INFORMATION: N-Et-Phe (N-ethyl phenylalanine)

<400> SEQUENCE: 23

Tyr Xaa Xaa Phe
1

<210> SEQ ID NO 24
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Orn (D-Ornithine)
<220> FEATURE:
<221> NAME/KEY: MISC_FEATURE
<222> LOCATION: (3)..(3)
<223> OTHER INFORMATION: N-Et-Phe (N-ethyl phenylalanine)
```

```
<400> SEQUENCE: 24

Tyr Xaa Xaa Phe
1

<210> SEQ ID NO 25
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Lys (D-Lysine)
<220> FEATURE:
<221> NAME/KEY: MISC_FEATURE
<222> LOCATION: (3)..(3)
<223> OTHER INFORMATION: N-Me-Phe (N-methyl phenylalanine)
<220> FEATURE:
<221> NAME/KEY: MISC_FEATURE
<222> LOCATION: (4)..(4)
<223> OTHER INFORMATION: D-Phe (D-phenylalanine)

<400> SEQUENCE: 25

Tyr Xaa Xaa Xaa
1

<210> SEQ ID NO 26
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: D-Lys (D-Lysine)
<220> FEATURE:
<221> NAME/KEY: MISC_FEATURE
<222> LOCATION: (3)..(3)
<223> OTHER INFORMATION: N-Et-Phe (N-ethyl phenylalanine)
<220> FEATURE:
<221> NAME/KEY: MISC_FEATURE
<222> LOCATION: (4)..(4)
<223> OTHER INFORMATION: D-Phe (D-phenylalanine)

<400> SEQUENCE: 26

Tyr Xaa Xaa Xaa
1
```

ANALGESIC MU-OPIOID RECEPTOR BINDING PEPTIDE PHARMACEUTICAL FORMULATIONS AND USES THEREOF

CROSS-REFERENCE TO A RELATED APPLICATION

This application claims the priority benefit of U.S. Provisional Application Ser. No. 62/524,491, filed Jun. 24, 2017, and U.S. Provisional Application Ser. No. 62/592,601, filed Nov. 30, 2017; both of which are incorporated herein by reference in their entirety.

SEQUENCE LISTING

The Sequence Listing for this application is labeled "SeqList-02Apr18-ST25.txt," which was created on Apr. 2, 2018, and is 8 KB. The Sequence Listing is incorporated herein by reference in its entirety.

BACKGROUND OF THE INVENTION

The major function for opiates is their role in alleviating pain. Other areas where opiates are well-suited for use are conditions relating to gastrointestinal disorders, schizophrenia, obesity, blood pressure, convulsions, and seizures.

Three different opiate receptors have been found: delta (δ), kappa (κ) and mu (μ). Endomorphin-1 peptide (EM-1) and its analogs have been found to exhibit opiate-like activity by binding to the μ opiate receptor.

Activation of the μ receptor is among the most effective means of alleviating a wide range of pain conditions. The unique effectiveness of μ agonists can be attributed to several factors, including their presence in numerous regions of the nervous system that regulate pain processing and activation of multiple mechanisms that limit pain transmission (e.g., inhibiting release of excitatory transmitters from the peripheral nervous system and decreasing cellular excitability in the central nervous system).

Limitations on the use of opioids result from negative side effects, including abuse liability, respiratory depression, and cognitive and motor impairment. Major efforts to develop compounds that maintain analgesic properties while reducing the negative side effects have met with limited success. This is evident from the current epidemic of prescription drug abuse.

Over 100 million patients annually in the United States experience acute or chronic pain and frequently do not achieve adequate relief from existing drugs due to limited efficacy and/or excessive side effects.

Because morphine and other compounds with clinical usefulness act primarily at the μ receptor, pharmaceutical compositions having peptides with high affinity and selectivity for this site are of considerable importance. It would therefore be desirable to have pharmaceutical formulations for delivering these compounds.

Natural endogenous peptides from bovine and human brain that are highly selective for the μ opioid receptor relative to the delta or kappa receptor have been described (see, for example, U.S. Pat. No. 6,303,578, which is incorporated herein by reference in its entirety). These peptides are potent analgesics and have shown promise of reduced abuse liability and respiratory depression.

Cyclized, D-amino acid-containing tetrapeptide analogs of the endomorphins (U.S. Pat. No. 5,885,958, which is incorporated herein by reference in its entirety) have also been described. While these results are promising, the development of improved pharmaceutically-acceptable formulations is needed.

Some currently available opioid formulations are too dilute to meet the needs of patients requiring long term treatment or large drug doses to control pain. For example, sufentanil citrate is currently available in an aqueous solution at a concentration of 50 μg/mL; morphine at 1 μg/mL; morphine sulfate at 20 μg/mL; fentanyl citrate at 20 μg/mL and alfentanil at 500 μg/mL. Simply adding more drug to conventional aqueous formulations is not a viable option to create more concentrated formulations as the opioid compound, especially those that are lipophilic such as fentanyl and its congeners, may precipitate out of solution, which leads to, for example, inconsistent delivery rates, reduced drug absorption, reduced tissue response and clogging of the drug delivery device or other points along the infusion pathway.

The subject invention addresses this need by providing new and advantageous peptide formulations having improved solubility and other properties.

BRIEF SUMMARY OF THE INVENTION

The subject invention provides compositions and methods for alleviating pain. Specifically, the subject invention provides pharmaceutical formulations of peptides, and/or their salts, having advantageous μ-opioid receptor binding activity.

In preferred embodiments of the subject invention, the peptide is SEQ ID NO: 13: H-Tyr$^1$-cyclo-(D-Lys$^2$-Trp$^3$-Phe$^4$) i.e., amino acids: Tyrosine, Lysine, Tryptophan, and Phenylalanine.

In preferred embodiments, the composition is an aqueous formulation prepared by mixing a salt of the peptide with a cyclodextrin.

The cyclodextrin may be, for example, α-Cyclodextrin, β-Cyclodextrin, 2-Hydroxypropyl-β-cyclodextrin, Methylated β-cyclodextrin, Sulfobutylether β-cyclodextrin, or 2-Hydroxypropyl-γ-cyclodextrin. In a further preferred embodiment, the cyclodextrin is 2-Hydroxypropyl-β-cyclodextrin.

In other embodiments, the peptide may be formulated with, for example, propylene glycol, chremophor, polyethylene glycol and/or polysorbate.

The salt of SEQ ID NO: 13 may be, for example, hydrochloride, maleate, acetate, tartrate, or aspartate salt. The peptide may also be present as a free base.

In a specific embodiment, the formulation contains 20% (w/v) hydroxypropyl-β-cyclodextrin (HPβCD), approximately 0.01 N HCl and 6 mg/mL SEQ ID NO: 13, at a final pH 4.75-5.25.

The formulation may be a suspension or a solution. In preferred embodiments, the formulation is a solution.

Formulations of the subject invention can also be used with peptides other than SEQ ID NO: 13 that have μ-opioid receptor binding activity. These peptides may be, for example, any of SEQ ID NO: 1 to 26. The opioid peptide may also be any of those disclosed in U.S. Patent Application Nos. 2012/0322740 A1, US 2013/0178427 A1, US 2015/0315238 A1, US 2016/0009764 A1, US 2016/0176930 A1 or US 2016/0264625 A1. Each of these applications is incorporated herein, by reference, in its entirety.

Another aspect of the subject invention is directed to the use of the compositions in a method of treating a patient having a condition that responds to an entity that binds to the μ-opioid receptor. Such a method comprises administering to the patient an effective amount of a pharmaceutical composition of the subject invention.

Particular embodiments of this method can be performed for the purpose of providing at least one effect selected from (i) analgesia (pain relief), (ii) relief from a gastrointestinal disorder such as diarrhea, (iii) therapy for an opioid drug dependence, (iv) neuropathic pain, and (v) treatment of any condition for which an opioid is indicated.

In some embodiments, the pharmaceutical compositions of the subject invention can be used to treat acute or chronic pain. Uses for the compositions also include, but are not limited to, use as antimigraine agents, immunomodulatory agents, immunosuppressive agents and/or antiarthritic agents.

Certain embodiments of the methods of the present invention, such as treatment of pain or opioid drug dependence, are directed to patients having a history of opioid substance abuse.

In certain embodiments of the present methods, the composition of the subject invention is administered parenterally. The administration may be done by, for example, intravenous, intramuscular, or subcutaneous administration. In other embodiments, the composition is administered orally.

BRIEF DESCRIPTION OF THE SEQUENCES

SEQ ID NO:1 is a peptide useful according to the subject invention.

SEQ ID NO:2 is a peptide useful according to the subject invention.

SEQ ID NO:3 is a peptide useful according to the subject invention.

SEQ ID NO:4 is a peptide useful according to the subject invention.

SEQ ID NO:5 is a peptide useful according to the subject invention.

SEQ ID NO:6 is a peptide useful according to the subject invention.

SEQ ID NO:7 is a peptide useful according to the subject invention.

SEQ ID NO:8 is a peptide useful according to the subject invention.

SEQ ID NO:9 is a peptide useful according to the subject invention.

SEQ ID NO:10 is a peptide useful according to the subject invention.

SEQ ID NO:11 is a peptide useful according to the subject invention.

SEQ ID NO:12 is a peptide useful according to the subject invention.

SEQ ID NOS:13-26 are additional peptides useful according to the subject invention.

DETAILED DESCRIPTION OF THE INVENTION

The subject invention provides compositions and methods for alleviating pain. Specifically, the subject invention provides pharmaceutical formulations of peptides, and/or their salts, having advantageous μ-opioid receptor binding activity. Advantageously, the concentration of the peptide in the formulation of the subject invention can be at or above 1, 2, 3, 4, 5, 6, 7, 8, 9, or even 10 mg/ml. In preferred embodiments, the formulation is a solution.

In preferred embodiments of the subject invention, the peptide is SEQ ID NO: 13: H-Tyr$^1$-cyclo-(D-Lys$^2$-Trp$^3$-Phe$^4$) i.e., amino acids: Tyrosine, Lysine, Tryptophan, and Phenylalanine.

In preferred embodiments the composition is an aqueous formulation of the peptide with a cyclodextrin.

The cyclodextrin may be, for example, α-Cyclodextrin, β-Cyclodextrin, 2-Hydroxypropyl-β-cyclodextrin, Methylated β-cyclodextrin, Sulfobutylether β-cyclodextrin, or 2-Hydroxypropyl-γ-cyclodextrin. In further preferred embodiments, the cyclodextrin is 2-Hydroxypropyl-3-cyclodextrin. The concentration of cyclodextrin may be, for example, from 5% to 40%, 10% to 35%, or 15% to 25%.

The composition can be formed by, for example, combining a salt of the peptide with the cyclodextrin in an aqueous solution.

The salt of the peptide may be, for example, hydrochloride, maleate, acetate, tartrate, or aspartate salt. The peptide may also be present as the free base.

In a specific embodiment the formulation contains 20% (w/v) hydroxypropyl-β-cyclodextrin (HPBCD), approximately 0.01 N HCl and 6 mg/mL SEQ ID NO: 13, at a final pH 4.75-5.25.

In other embodiments, the peptide may be formulated with, for example, propylene glycol, chremophor, polyethylene glycol and/or polysorbate.

The formulation may be a suspension or a solution. In preferred embodiments, the formulation is a solution.

Formulations of the subject invention can also be used with opioid peptides other than SEQ ID NO: 13. These opioid peptides may be, for example, any of SEQ ID NO: 1 to 26. The opioid peptide may also be any of those disclosed in U.S. Patent Application Nos. 2012/0322740 A1, US 2013/0178427 A1, US 2015/0315238 A1, US 2016/0009764 A1, US 2016/0176930 A1 or US 2016/0264625 A1. Each of which patent applications is incorporated herein, by reference, in its entirety.

Peptides that can be used according to the subject invention include those having the general formula Tyr-$X_1$-$X_2$-$X_3$ wherein $X_1$ is Pro, D-Lys or D-Orn; $X_2$ is Trp, Phe or N-alkyl-Phe wherein alkyl contains 1 to about 6 carbon atoms; and $X_3$ is Phe, Phe-NH$_2$, D-Phe, D-Phe-NH$_2$ or p-Y-Phe wherein Y is NO$_2$, F, Cl or Br. Some specific peptides of the invention are:

| | |
|---|---|
| H-Tyr-Pro-Trp-Phe-NH$_2$ | (SEQ ID NO: 1) |
| H-Tyr-Pro-Phe-Phe-NH$_2$ | (SEQ ID NO: 2) |
| H-Tyr-Pro-Trp-Phe-OH | (SEQ ID NO: 3) |
| H-Tyr-Pro-Phe-Phe-OH | (SEQ ID NO: 4) |
| H-Tyr-Pro-Trp-D-Phe-NH$_2$ | (SEQ ID NO: 5) |
| H-Tyr-Pro-Phe-D-Phe-NH$_2$ | (SEQ ID NO: 6) |
| H-Tyr-Pro-Trp-pNO$_2$-Phe-NH$_2$ | (SEQ ID NO: 7) |
| H-Tyr-Pro-Phe-pNO$_2$-Phe-NH$_2$ | (SEQ ID NO: 8) |
| H-Tyr-Pro-N-Me-Phe-Phe-NH$_2$ | (SEQ ID NO: 9) |
| H-Tyr-Pro-N-Et-Phe-Phe-NH$_2$ | (SEQ ID NO: 10) |
| H-Tyr-Pro-N-Me-Phe-D-Phe-NH$_2$ | (SEQ ID NO: 11) |
| H-Tyr-Pro-N-Et-Phe-D-Phe-NH$_2$ | (SEQ ID NO: 12) |
| H-Tyr-c-[D-Lys-Trp-Phe] | (SEQ ID NO: 13) |

```
H-Tyr-c-[D-Lys-Phe-Phe]           (SEQ ID NO: 14)

H-Tyr-c-[D-Orn-Trp-Phe]           (SEQ ID NO: 15)

H-Tyr-c-[D-Orn-Phe-Phe]           (SEQ ID NO: 16)

H-Tyr-c-[D-Lys-Trp-pNO2-Phe]      (SEQ ID NO: 17)

H-Tyr-c-[D-Lys-Phe-pNO2-Phe]      (SEQ ID NO: 18)

H-Tyr-c-[D-Orn-Trp-pNO2-Phe]      (SEQ ID NO: 19)

H-Tyr-c-[D-Orn-Phe-pNO2-Phe]      (SEQ ID NO: 20)

H-Tyr-c-[D-Lys-N-Me-Phe-Phe]      (SEQ ID NO: 21)

H-Tyr-c-[D-Orn-N-Me-Phe-Phe]      (SEQ ID NO: 22)

H-Tyr-c-[D-Lys-N-Et-Phe-Phe]      (SEQ ID NO: 23)

H-Tyr-c-[D-Orn-N-Et-Phe-Phe]      (SEQ ID NO: 24)

H-Tyr-c-[D-Lys-N-Me-Phe-D-Phe]    (SEQ ID NO: 25)

H-Tyr-c-[D-Lys-N-Et-Phe-D-Phe]    (SEQ ID NO: 26)
```

The last fourteen peptides listed are cyclic peptides whose linear primary amino acid sequences are given in SEQ ID NO:13 through SEQ ID NO: 26. In this context, the applicants incorporate herein by reference, in its entirety, U.S. Pat. No. 6,303,578.

Another aspect of the invention is directed to the use of the compositions described herein in a method of treating a patient having a condition that responds to an entity that binds to the μ-opioid receptor. Such a method comprises administering to the patient an effective amount of a pharmaceutical composition of the subject invention.

Particular embodiments of this method can be followed for the purpose of providing at least one effect selected from (i) analgesia (pain relief), (ii) relief from a gastrointestinal disorder such as diarrhea, (iii) therapy for an opioid drug dependence, (iv) neuropathic pain, and (v) treatment of any condition for which an opioid is indicated.

In some embodiments the pharmaceutical compositions of the subject invention can be used to treat acute or chronic pain. Uses for the compositions also include, but are not limited to, use as antimigraine agents, immunomodulatory agents, immunosuppressive agents and/or antiarthritic agents.

Certain embodiments of the methods of the present invention, such as treatment of pain or opioid drug dependence, are directed to patients having a history of opioid substance abuse.

In certain embodiments of the present methods, the composition of the subject invention is administered parenterally. The administration may be done by, for example, intravenous, intramuscular, or subcutaneous administration. In other embodiments, the composition is administered orally.

The pharmaceutical compositions can be delivered in any suitable dosage form, such as, for example, a liquid, gel, solid, cream, or paste dosage form. In one embodiment, the compositions can be adapted to give sustained release of the peptide.

The pharmaceutical compositions include, but are not limited to, those forms suitable for oral, rectal, nasal, topical, (including buccal and sublingual), transdermal, vaginal, parenteral (including intramuscular, subcutaneous, and intravenous), spinal (epidural, intrathecal), and central (intracerebroventricular) administration. The compositions can, where appropriate, be conveniently provided in discrete dosage units.

Selected Definitions

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

As used herein, the terms "reducing," "inhibiting," "blocking," "preventing", alleviating," or "relieving" when referring to a compound (e.g., a peptide), mean that the compound brings down the occurrence, severity, size, volume, or associated symptoms of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the condition, event, or activity would normally exist without application of the compound or a composition comprising the compound. The terms "increasing," "elevating," "enhancing," "upregulating," "improving," or "activating" when referring to a compound mean that the compound increases the occurrence or activity of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, 100%, 150%, 200%, 250%, 300%, 400%, 500%, 750%, or 1000% compared to how the condition, event, or activity would normally exist without application of the compound or a composition comprising the compound.

The term "modulating" includes "reducing," "inhibiting," "blocking," "preventing", alleviating," "relieving," "increasing," "elevating," "enhancing," "upregulating," "improving," and "activating."

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition.

Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

"Compounds of the present invention," and equivalent expressions, are meant to embrace the exemplified compounds as described herein, which expression includes the pharmaceutically acceptable salts, and solvates, e.g., hydrates, where the context so permits.

Such compounds can be formulated as pharmaceutical compositions and administered to a subject in need of treatment, for example a mammal, such as a human patient, in a variety of forms adapted to the chosen route of administration. For example compounds of the invention may be formulated for administration, orally, nasally, intraperitoneally, or parenterally, by intravenous, intramuscular, topical, or subcutaneous routes, or by injection into tissue.

Routes of Administration and Dosage Forms

In certain embodiments, the compounds may be administered intravenously or intraperitoneally by infusion or injection. Solutions of the compounds can be prepared in water, optionally mixed with a nontoxic surfactant. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds that are adapted for the extemporaneous preparation of sterile injectable or infusible solutions or dispersions, optionally encapsulated in liposomes. Preferably, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained by, for example, the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent as described herein with various of the other ingredients enumerated herein, as required, preferably followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

The compositions of the subject invention may also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet.

For oral therapeutic administration, the compounds may be combined with one or more excipients and used in the form of ingestible tablets, buccal tablets, troches, capsules, elixirs, suspensions, syrups, wafers, and the like. Such compositions and preparations should contain at least 0.1% of a compound of the present invention. The percentage of the compound of the invention present in such compositions and preparations may, of course, be varied and may conveniently be between about 2% to about 60% of the weight of a given unit dosage form. The amount of the compound in such therapeutically useful compositions is such that an effective dosage level will be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol.

Various other materials may be present as coatings or for otherwise modifying the physical form of the solid unit dosage form. For instance, tablets, pills, or capsules may be coated with gelatin, wax, shellac, or sugar, and the like. A syrup or elixir may contain the active compound, sucrose or fructose as a sweetening agent, methyl and propylparabens as preservatives, a dye, and flavoring such as cherry or orange flavor.

Of course, any material used in preparing any unit dosage form should be pharmaceutically acceptable and substantially non-toxic in the amounts employed.

In addition, the compounds may be incorporated into sustained-release preparations and devices. For example, the compounds may be incorporated into time release capsules, time release tablets, time release pills, and time release polymers or nanoparticles.

Pharmaceutical compositions for topical administration of the peptides to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for topical administration in the mouth (e.g., buccal or sublingual administration) include lozenges comprising the composition in a flavored base, such as sucrose, acacia, or tragacanth; pastilles comprising the composition in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

The concentration of the therapeutic compounds of the invention in such formulations can vary widely depending on the nature of the formulation and intended route of administration. For example, the concentration of the compounds in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Pharmaceutical compositions for spinal administration or injection into amniotic fluid can be provided in unit dose form in ampoules, pre-filled syringes, small volume infusion, or in multi-dose containers, and can include an added preservative. The compositions for parenteral administration can be suspensions, solutions, or emulsions, and can contain excipients such as suspending agents, stabilizing agents, and dispersing agents.

A pharmaceutical composition suitable for rectal administration comprises a peptide of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art.

According to one embodiment, pharmaceutical compositions of the present invention suitable for vaginal administration are provided as pessaries, tampons, creams, gels, pastes, foams, or sprays containing a peptide of the invention in combination with carriers as are known in the art. Alternatively, compositions suitable for vaginal administration can be delivered in a liquid or solid dosage form.

Pharmaceutical compositions suitable for intra-nasal administration are also encompassed by the present invention. Such intra-nasal compositions comprise a peptide of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the peptide. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the peptide.

The compounds may be combined with an inert powdered carrier and inhaled by the subject or insufflated.

Pharmaceutical compositions for administration by inhalation or insufflation can be provided in the form of a dry powder composition, for example, a powder mix of the peptide and a suitable powder base such as lactose or starch. Such powder composition can be provided in unit dosage form, for example, in capsules, cartridges, gelatin packs, or blister packs, from which the powder can be administered with the aid of an inhalator or insufflator.

The exact amount (effective dose) of the agent will vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The compounds can be conveniently administered in unit dosage form, containing for example, about 0.05 to about 10000 mg, about 0.5 to about 10000 mg, about 5 to about 1000 mg, or about 50 to about 500 mg of active ingredient per unit dosage form.

The compounds can be administered to achieve peak plasma concentrations of, for example, from about 0.25 to about 200 µM, about 0.5 to about 75 µM, about 1 to about 50 µM, about 2 to about 30 µM, or about 5 to about 25 µM. Exemplary desirable plasma concentrations include at least 0.25, 0.5, 1, 5, 10, 25, 50, 75, 100 or 200 µM. For example, plasma levels may be from about 1 to about 100 micromolar or from about 10 to about 25 micromolar. This may be achieved, for example, by the intravenous injection of a 0.05 to 5% solution of the compounds, optionally in saline, or orally administered as a bolus containing about 1 to about 100 mg of the compounds. Desirable blood levels may be maintained by continuous or intermittent infusion.

SEQ ID NO: 13 or other µ-opioid binding peptides will be included in the compositions within a therapeutically useful and effective concentration range, as determined by routine methods that are well known in the medical and pharmaceutical arts. For example, a typical composition can include one or more of the peptide at a concentration in the range of at least about 1 mg/ml, preferably at least about 4 mg/ml, more preferably at least 5 mg/ml and most preferably at least 6 mg/ml.

The compounds may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with a peptide of the present invention.

Methods of Treatment

The present invention provides for the use of the compositions of the subject invention for treatment of conditions that can be improved through binding at the µ-opioid receptor. This can include, for example, pain, discomfort associated with gastrointestinal disorders, and treatment of drug dependence.

Methods for providing analgesia (alleviating or reducing pain), relief from gastrointestinal disorders such as diarrhea, and therapy for drug dependence in patients, such as mammals, including humans, comprise administering to a patient suffering from one of the aforementioned conditions an effective amount of the composition of the subject invention.

Diarrhea may be caused by a number of sources, such as infectious disease, cholera, or an effect or side-effect of various drugs or therapies, including those used for cancer therapy. Preferably, the peptide is administered parenterally or enterally. The dosage of the effective amount of the peptides can vary depending upon the age and condition of each individual patient to be treated. However, suitable unit dosages typically range from about 0.01 to about 100 mg. For example, a unit dose can be in the range of about 0.2 mg to about 50 mg. Such a unit dose can be administered more than once a day, e.g., two or three times a day.

The following examples are included to demonstrate certain aspects of the invention. It should be appreciated by those of skill in the art that the techniques disclosed in the examples, which represent techniques known to function well in practicing the invention, can be considered to constitute preferred modes for its practice; however, those of skill in the art should, in light of the present disclosure, appreciate that many changes can be made in the specific disclosed embodiments and still obtain a like or similar result without departing from the spirit and scope of the invention. The examples, thus, are provided for illustration purposes only and are not intended to be limiting.

Example 1: Preparation of a SEQ ID NO: 13 Composition of the Subject Invention

A formulation is prepared that includes SEQ ID NO: 13, 20% HPBCD, and approximately 0.01N HCl made in sterile water by the following method.

First, the HPβCD and HCl are added to sterile water. SEQ ID NO: 13 is added at 7.5 mg/mL. The mixture is stirred overnight at room temperature and then filtered through 0.45 µm filter to remove any insoluble material.

The in-process concentration is determined by HPLC analysis.

The filtered solution is then diluted (with 20% HPβCD solution without HCl) to 6 mg/mL SEQ ID NO: 13 after analysis and filtered again through 0.22 μm filters.

Example 2: Ingredients of a SEQ ID NO: 13 Composition of the Subject Invention

Table 1 shows the ingredients of a preferred embodiment of the composition of the subject invention.

TABLE 1

| Component | Quantity per mL | % |
| --- | --- | --- |
| SEQ ID NO: 13[+] | 6.1 mg | 0.61% (w/v) |
| HCl USP | 0.365 mg* (10 μmol) | 0.036% (w/v)* (10 mM) |
| HPβCD, USP | 200 mg | 20% (w/v) |
| Water for Injection, USP/EP | To 1.0 mL | To 100% |

[+]Corrected for Peptide and Purity Content
Peptide Content = 97.4%
Purity (HPLC) = 99.7%
*maximum HCl level based on final pH 4.75-5.25

Example 3: Additional Formulations

TABLE 5

Additional SEQ ID NO: 13 formulations showing antinococeptive activity in the rat tail flick assay

| | |
| --- | --- |
| 20% 2-Hydroxypropyl-B-cyclodextrin | 0.01N HCl |
| 20% 2-Hydroxypropyl-B-cyclodextrin | |
| 40% Propylene Glycol | 0.01N HCl |
| 40% Propylene Glycol | 0.02N Acetic Acid |
| 40% Propylene Glycol | 0.02N Na Citrate, pH 3 |
| 20% PEG-300 | 0.02N Acetic Acid |
| 10% Chremophor RH60 | 0.01N HCl |
| 10% Chremophor RH60 | 0.02N Acetic |
| 10% Chremophor EL | 0.01N HCl |
| 10% Chremophor EL | 0.02N Acetic |
| 10% Polysorbate 80 | 0.01N HCl |
| 10% Polysorbate 80 | 0.02N Acetic |

All documents, references, and information, including, but not limited to, journal articles, patent applications, and patents, that are mentioned, cited, or referred to in this application are hereby incorporated by reference in their entirety.

The invention claimed is:
1. A composition having μ-opioid receptor binding activity wherein the composition is an aqueous solution that comprises the acetate salt of a μ-opioid receptor binding peptide and a cyclodextrin, wherein the cyclodextrin is 2-Hydroxypropyl-β-cyclodextrin (HPβC) at a concentration from 15% to 25%, the composition comprises about 0.01 N HCl and has a pH from 4.75-5.25, and wherein the concentration of the peptide is about 6.1 mg/ml, and wherein the peptide is SEQ ID NO: 13.

* * * * *

UNITED STATES PATENT AND TRADEMARK OFFICE
CERTIFICATE OF CORRECTION

PATENT NO. : 10,975,121 B2
APPLICATION NO. : 15/962200
DATED : April 13, 2021
INVENTOR(S) : Theodore E. Maione and Constantine Basil Maglaris It is certified that error appears in the above-identified patent and that said Letters Patent is hereby corrected as shown below:

In the Specification

Column 4:
Lines 11-12, "2-Hydroxypropyl-3-cyclodextrin" should read -- 2-Hydroxypropyl-β-cyclodextrin --.
Line 21, "(HPBCD)," should read -- (HPβCD), --.
Line 40, "D-Lys or D-Om;" should read -- D-Lys or D-Orn; --.

Column 12:
Line 60, "20% HPBCD," should read -- 20% HPβCD, --.

Signed and Sealed this
Third Day of August, 2021

Drew Hirshfeld
*Performing the Functions and Duties of the
Under Secretary of Commerce for Intellectual Property and
Director of the United States Patent and Trademark Office*